(12) United States Patent
Shue et al.

(10) Patent No.: US 7,425,205 B2
(45) Date of Patent: Sep. 16, 2008

(54) DISPOSABLE SYRINGE WITH A RETRACTABLE NEEDLE

(76) Inventors: Ming-Jeng Shue, No. 14, Lane 8, Chung-I St., Hsi Dist., Taichung City (TW); Deborah Huang, 7F, No. 5, Sec. 3, Liu-Chun E. St., Chung Dist., Taichung City (TW); Phillip Shue, No. 14, Lane 8, Chung-I St., Hsi Dist., Taichung City (TW)

( * ) Notice: Subject to any disclaimer, the term of this patent is extended or adjusted under 35 U.S.C. 154(b) by 430 days.

(21) Appl. No.: 10/918,020

(22) Filed: Aug. 13, 2004

(65) Prior Publication Data

US 2006/0100577 A1 May 11, 2006

(30) Foreign Application Priority Data

Apr. 30, 2004 (TW) .............................. 93112143 A

(51) Int. Cl.
*A61M 5/00* (2006.01)
(52) U.S. Cl. .................................................... 604/110
(58) Field of Classification Search ................. 604/110, 604/181, 187, 192, 194–196, 218, 240
See application file for complete search history.

(56) References Cited

U.S. PATENT DOCUMENTS

| 5,084,018 | A | 1/1992 | Tsao |
| 5,211,628 | A | 5/1993 | Marshall |
| 5,395,337 | A * | 3/1995 | Clemens et al. ............. 604/110 |
| 2003/0236501 | A1 | 12/2003 | Donnan et al. |
| 2004/0015129 | A1* | 1/2004 | Shue et al. .................. 604/110 |

FOREIGN PATENT DOCUMENTS

| EP | 1 421 962 | 5/2004 |
| EP | 1421962 | * 5/2004 |

OTHER PUBLICATIONS

European Search Report dated Jan. 19, 2005 corresponding to European Patent Application No. 04 25 4805.

* cited by examiner

*Primary Examiner*—Kevin C. Sirmons
*Assistant Examiner*—Catherine N. Witczak
(74) *Attorney, Agent, or Firm*—Ohlandt, Greeley, Ruggiero & Perle, L.L.P.

(57) ABSTRACT

A disposable syringe includes a barrel having a retaining region to retain a needle seat for carrying a needle cannula, and a friction diminishing region extending forwardly from the retaining region and terminating at a shoulder abutment, a plunger movable in the barrel toward the needle seat, and a coupling member biased by a biasing member and having a retained portion to frictionally engage the plunger, and an anchored portion to engage an anchoring portion of the needle seat such that when the needle seat is moved past the friction diminishing region to abut against the shoulder abutment, a subsequent pushing force applied to the plunger results in release of the retained portion from the plunger, thereby enabling the anchored portion to be moved into the plunger by means of the biasing member.

18 Claims, 25 Drawing Sheets

DISPOSABLE SYRINGE WITH A RETRACTABLE NEEDLE

BACKGROUND OF THE INVENTION

1. Field of the Invention

This invention relates to a disposable syringe, more particularly to a disposable syringe with a friction diminishing means for facilitating retraction of a needle into a tubular plunger.

2. Description of the Related Art

Conventional syringes, especially those with a sharp needle, have to be disposed safely after injection. Therefore, there are many syringes with a retractable needle that is retracted into a plunger when the plunger reaches the end of its stroke. However, it is desirable to improve the steady retracted movement of the syringe and the variety of the diameter of the syringe barrel.

SUMMARY OF THE INVENTION

The object of the present invention is to provide a disposable syringe which permits steady retraction of a plunger and which ensures successful retraction of a needle assembly.

According to this invention, the disposable syringe includes a needle cannula, a tubular needle seat, a barrel, a tubular grip member, a tubular plunger, a coupling member and a biasing member.

The tubular needle seat includes a front hub portion which is disposed to fix the needle cannula therein, a gripped portion which extends from the front hub portion in a longitudinal direction, and a rear anchoring portion which is disposed opposite to the front hub portion in the longitudinal direction.

The barrel has an inner surrounding barrel surface which surrounds an axis in the longitudinal direction and which defines a passage therein. The passage has rearward and forward openings opposite to each other in the longitudinal direction. The inner surrounding barrel surface includes a larger-diameter portion and a smaller-diameter portion which are disposed proximate to the rearward and forward openings, respectively. The larger-diameter portion has a retaining area which is spaced apart from the smaller-diameter portion in the longitudinal direction. The smaller-diameter portion includes a retaining region which is disposed proximate to the larger-diameter portion and which is configured to retain the front hub portion thereat when the needle seat is in a position of use, and a friction diminishing region which extends from the retaining region toward the forward opening and which terminates at a shoulder abutment. The shoulder abutment defines a communicating hole which permits passage of the needle cannula therethrough, and is spaced apart from the front hub portion along the axis in the position of use.

The tubular grip member, in the position of use, is disposed to bring the gripped portion into engagement with the retaining area by virtue of a first frictional force generated therebetween.

The tubular plunger is disposed to be movable in the passage along the larger-diameter portion. The plunger has a front opened end wall which is movable to abut against the grip member, a rear opened end wall which is disposed opposite to the front opened end wall and which extends outwardly of the rearward opening so as to be manually operable, and an intermediate surrounding wall which is interposed between the front and rear opened end walls and which defines an accommodation chamber.

The coupling member has a surrounding retained portion which surrounds the axis and which is disposed in the accommodation chamber to be in frictional engagement with the intermediate surrounding wall by virtue of a second frictional force, and an anchored portion which is disposed adjacent to the front opened end wall in the position of use, which confronts the rear anchoring portion, and which is engageable with the rear anchoring portion by a holding force when the coupling member is moved forwardly towards the forward opening. Thus, when the grip member is pushed by virtue of forward movement of the plunger against the first frictional force to move the front hub portion past the friction diminishing region to abut against the shoulder abutment, a pushing force subsequently applied to the plunger causes the anchored portion to rub against the rear anchoring portion, which remains unmoved in place due to engagement of the front hub portion with the shoulder abutment, so that the anchored portion is engaged with the rear anchoring portion and is moved relative to the intermediate surrounding wall towards the rear opened end wall so as to release the surrounding retained portion from the intermediate surrounding wall, thereby enabling the anchored portion to be moved from the position of use to a retracted position where the anchored portion is disposed closer to the rear opened end wall, and where the needle seat and the needle cannula are received in the accommodation chamber.

The biasing member is disposed to bias the anchored portion towards the retracted position.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
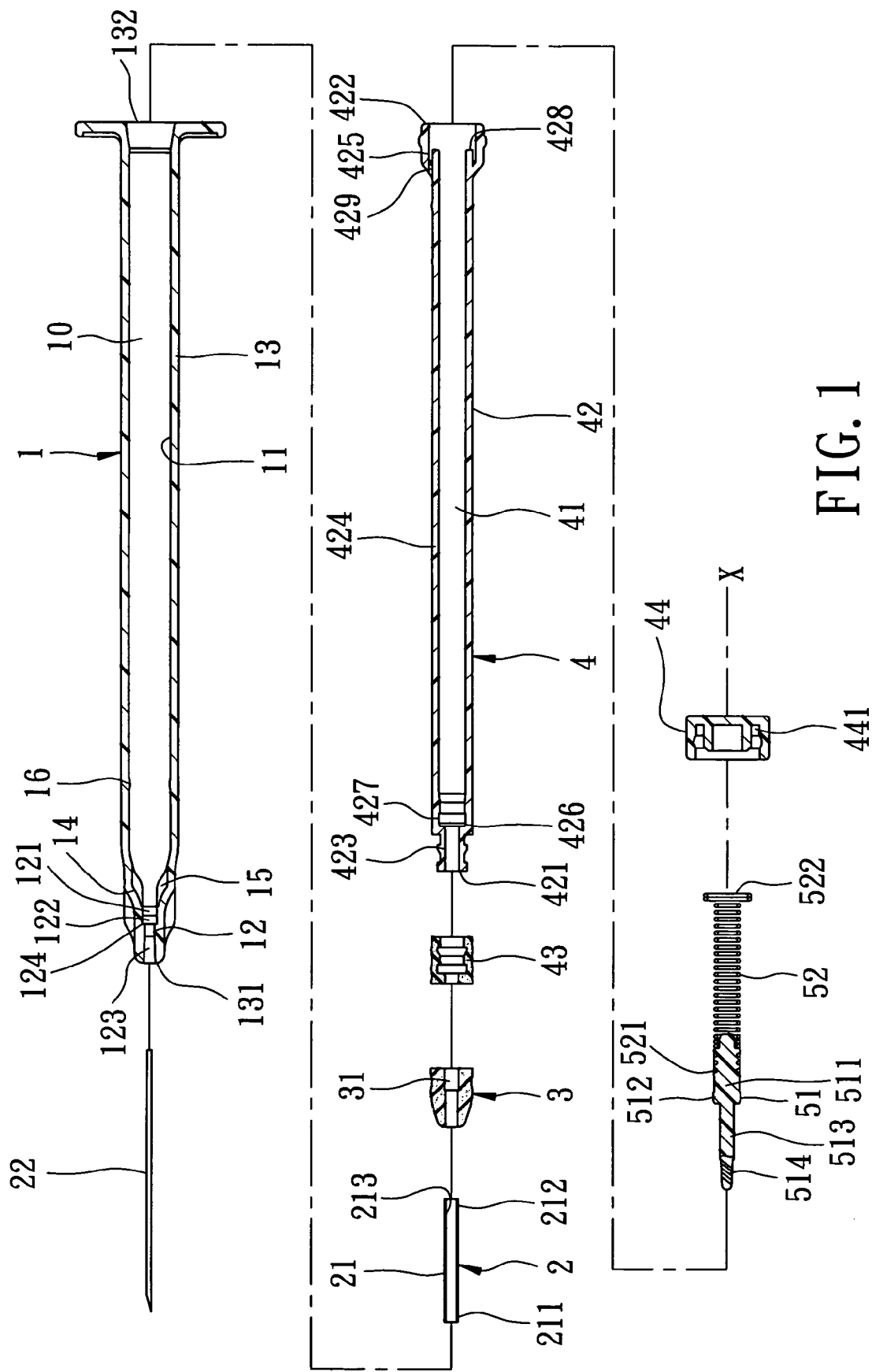
FIG. 1 is an exploded sectional view of the first preferred embodiment of a disposable syringe according to this invention.

Before the present invention is described in greater detail, it should be noted that same reference numerals have been used to denote like elements throughout the specification.

Figure 2:
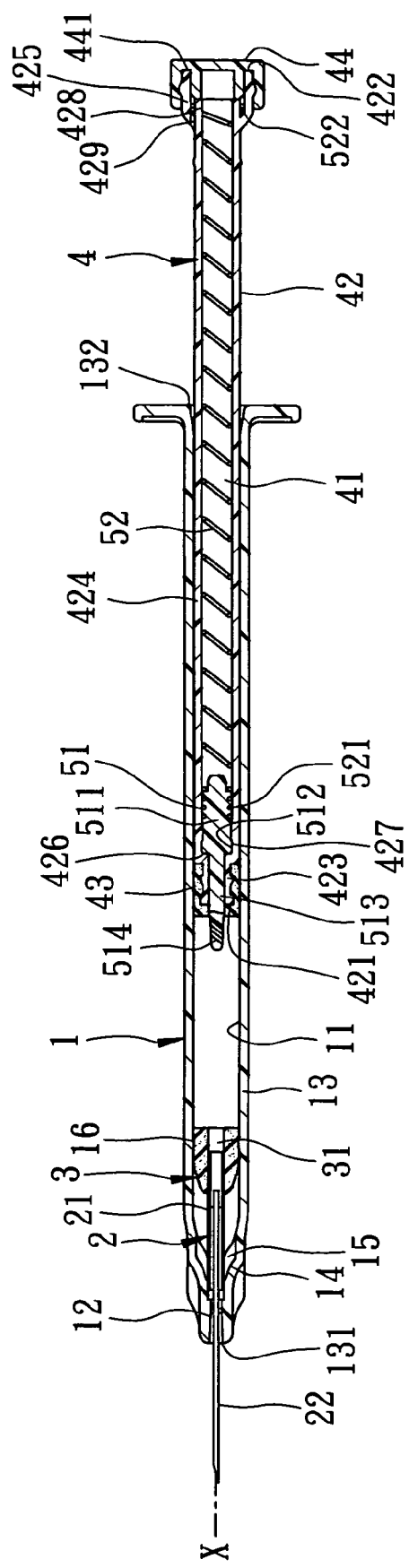
FIG. 2 is a sectional view of the first preferred embodiment in a state of use.

Referring to FIGS. 1 and 2, the first preferred embodiment of a disposable syringe according to the present invention is shown to comprise a needle assembly 2, a barrel 1, a tubular grip member 3, a tubular plunger 4, a coupling member 51, and a biasing member 52.

The needle assembly 2 includes a needle cannula 22 and a tubular needle seat 21. The needle seat 21 is in the form of a hard thin wall tube, such as a metal or carbon fiber tube which includes a front segment 211 to serve as a front hub portion 211 that is disposed to fix the needle cannula 22 therein, and a rear segment that extends from the front segment along an axis (X) in a longitudinal direction. The rear segment has outer and inner segment surfaces opposite to each other in radial directions relative to the axis (X) to serve as a gripped portion 212 and a rear anchoring portion 213, respectively.

The barrel 1 has an inner surrounding barrel surface 13 which surrounds the axis (X) in the longitudinal direction and which defines a passage 10 therein. The passage 10 has rearward and forward openings 132, 131 which are disposed opposite to each other in the longitudinal direction. The inner surrounding barrel surface 13 includes a larger-diameter portion 11 and a smaller-diameter portion 12 which are disposed proximate to the rearward and forward openings 132, 131, respectively, an annular shoulder 14 which converges gradually from the larger-diameter portion 11 to the smaller-diameter portion 12, and a plurality of ribs 15 which are formed on an inner surface of the shoulder 14 to retain a part of the front hub portion 211 of the needle seat 21. The larger-diameter portion 11 has a retaining area 16 which is in the form of an annular protrusion and which is spaced apart from the smaller-diameter portion 12 in the longitudinal direction.

The smaller-diameter portion 12 includes a retaining region 121 which is disposed in connection with the ribs 15 and which is configured to retain a part of the front hub portion 211 of the needle seat 21 thereat when the needle seat 21 is in a position of use, and a friction diminishing region 122 which extends from the retaining region 121 toward the forward opening 131 and which terminates at a shoulder abutment 124. The passage 10 at the friction diminishing region 122 has a diameter larger than that of the passage 10 at the retaining region 121. The shoulder abutment 124 defines a communicating hole 123 which is configured to permit passage of the needle cannula 22 therethrough, and is spaced apart from the front hub portion 211 along the axis (X) in the position of use.

In the position of use, the tubular grip member 3 is disposed, to bring the gripped portion 212 of the needle seat 21 into engagement with the retaining area 16 by virtue of a first frictional force generated therebetween. In particular, the grip member 3 is in fluid-tight and frictional engagement with the retaining area 16, and has an axially extending hole 31 for receiving the gripped portion 212.

The tubular plunger 4 is disposed to be movable in the passage 10 along the larger-diameter portion 11. The plunger 4 has a front opened end wall 421 which is movable to abut against the grip member 3, a rear opened end wall 422 which is disposed opposite to the front opened end wall 421 and which extends outwardly of the rearward opening 132 so as to be manually operable, and an intermediate surrounding wall 42 which is interposed between the front and rear opened end walls 421,422 and which defines an accommodation chamber 41. The intermediate surrounding wall 42 has a smaller front segment 423 and a larger rear segment 424 disposed proximate to the front and rear opened end walls 421,422, respectively, to form a shoulder 426 therebetween. An enlarged terminal segment 425 is disposed between the larger rear segment 424 and the rear opened end wall 422, and is formed with a vent hole 429 so as to be in fluid communication with the ambient atmosphere. An annular rib 428 is disposed between the larger rear segment 424 and the enlarged terminal segment 425, and extends in the longitudinal direction. An end cap 44 is disposed to cover the rear opened end wall 422, and has an annular groove 441 for engagement with the enlarged terminal segment 425. In addition, an annular groove 427 is formed in an inner peripheral surface of the larger rear segment 424 proximate to the shoulder 426. A seal ring 43, which is made of a deformable material, is sleeved retainingly over an outer peripheral surface of the smaller front segment 423 so as to be slidable on and to be in fluid-tight frictional engagement with both the larger-diameter portion 11 of the inner surrounding barrel surface 13 and the coupling member 51.

The coupling member 51 has a surrounding retained portion 512 which surrounds the axis (X) and which is in the form of an annular protrusion disposed to be in frictional engagement with the annular groove 427 in the intermediate surrounding wall 42 by virtue of a second frictional force, an anchored portion 514 which extends forwardly of the front opened end wall 421 in the position of use to confront the rear anchoring portion 213 so as to be engageable with the rear anchoring portion 213 by a holding force when the coupling member 51 is moved forwardly towards the forward opening 131, a retained shank portion 513 which is disposed between the surrounding retained portion 512 and the anchored portion 514 and which extends in the accommodation chamber 41 at the smaller front segment 423 so as to stabilize the coupling member 51 at the smaller front segment 423, and a shank portion 511 which extends from the surrounding retained portion 512 distal from the anchored portion 514.

The biasing member 52 is a coiled spring, and has a front spring end 521 which engages the shank portion 511, and a rear spring end 522 which is retained between the annular rib 428 and the intermediate surrounding wall 42 such that the coiled spring 52 is tensioned when the surrounding retained portion 512 is in frictional engagement with the annular groove 427 by virtue of the second frictional force, as shown in FIG. 2.

Figure 3:
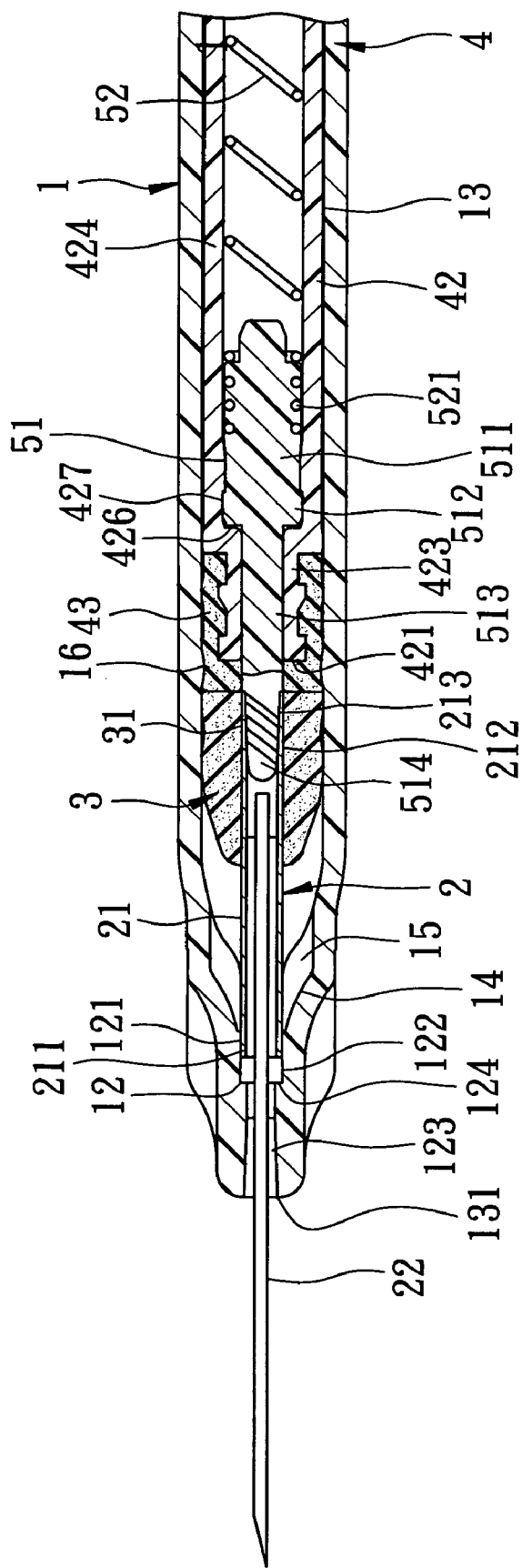
FIGS. 3 to 5 are fragmentary sectional views of the first preferred embodiment, showing a coupling member in three different states.
Figure 4:
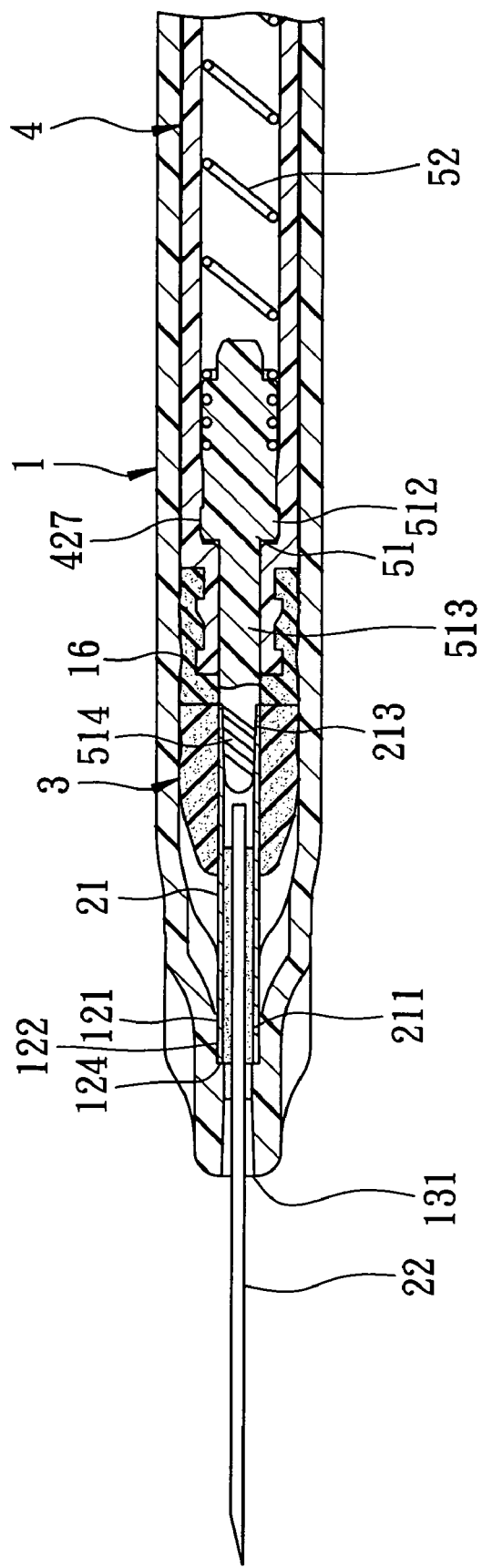
Figure 5:
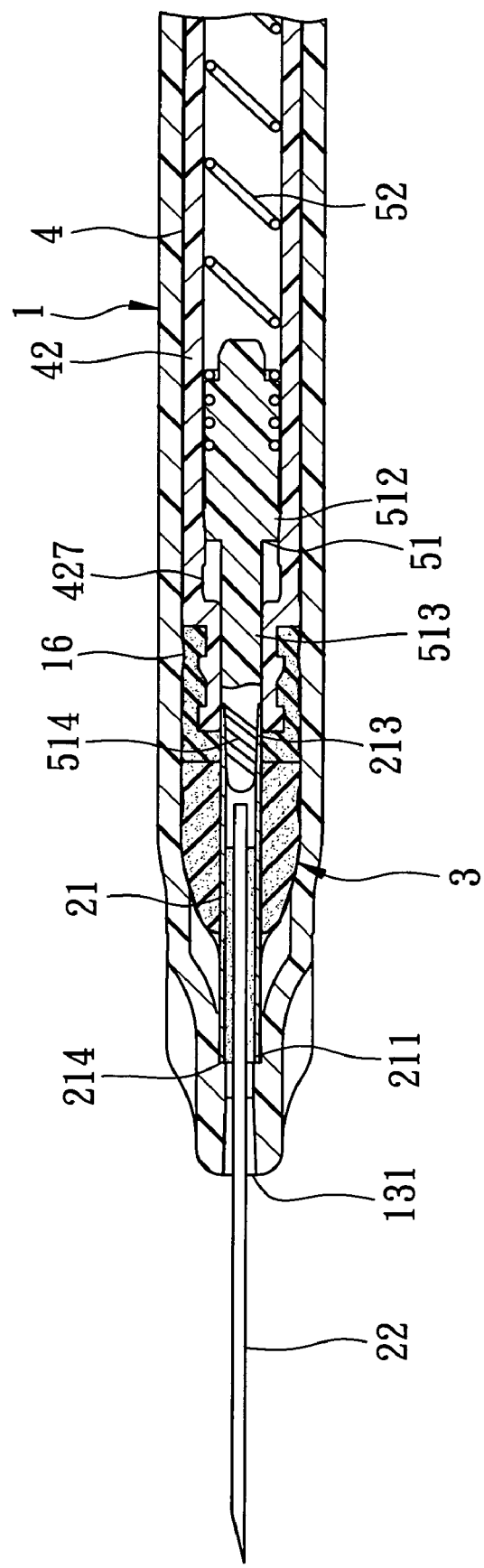
Figure 6:
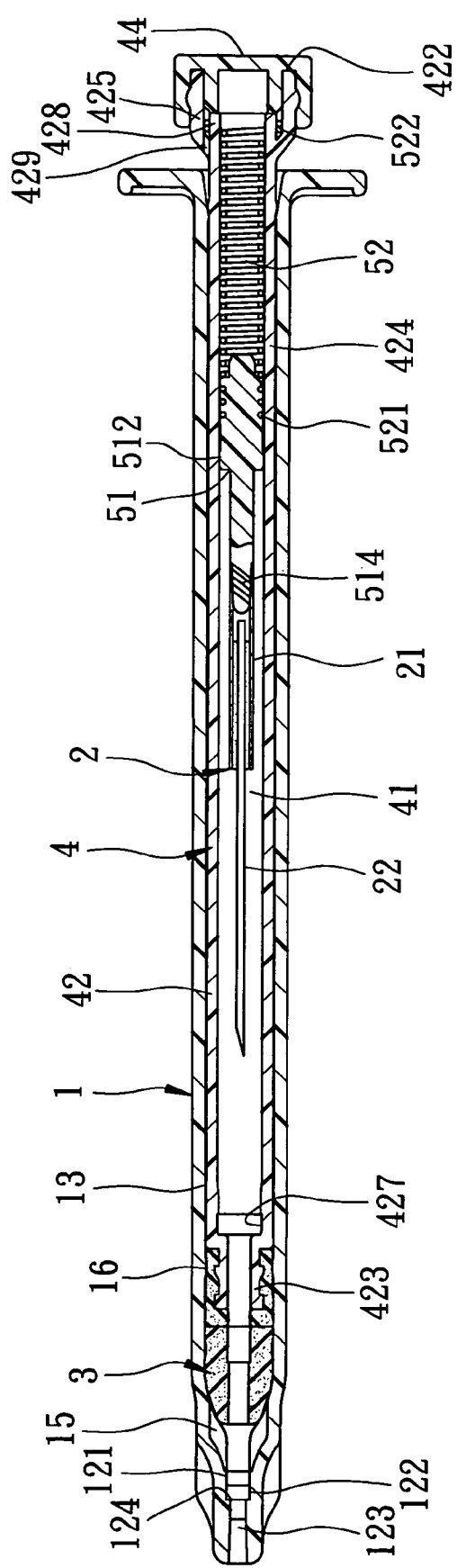
FIG. 6 is a sectional view of the first preferred embodiment in a retracted state.

After completion of an injection course, the plunger 4 is pressed forwardly by a pushing force to permit abutment of the seal ring 43 against the grip member 3. At this time, the anchored portion 514 is extended into the axially extending hole 31. Subsequently, with reference to FIGS. 3 and 4, a manual pushing force is further applied to the plunger 4 to push the grip member 3 forward against the first frictional force (i.e., the frictional engagement between the grip member 3 and the retaining area 16) such that the anchored portion 514 is partially extended into and engaged with the rear anchoring portion 213, and such that the front hub portion 211 moves past the friction diminishing region 122 to abut against the shoulder abutment 124. Meanwhile, the movement of the front hub portion 211 past the friction diminishing region 122 results in reduced friction therebetween. Therefore, as shown in FIG. 5, when a pushing force is subsequently applied to the plunger 4 to cause the anchored portion 514 to rub against the rear anchoring portion 213, which remains unmoved due to engagement of the front hub portion 211 with the shoulder abutment 124, the anchored portion 514 is engaged with the rear anchoring portion 213 and is moved relative to the intermediate surrounding wall 42 towards the rear opened end wall 422 so as to release the surrounding retained portion 512 from the annular groove 427 in the intermediate surrounding wall 42, thereby enabling the anchored portion 514 to be moved by the biasing force of the coiled spring 52 from the position of use to a retracted position where the anchored portion 514 is disposed closer to the rear opened end wall 422 and where the needle assembly 2 (i.e. the needle seat 21 and the needle cannula 22) is received in the accommodation chamber 41, as shown in FIG. 6.

It is noted that with the provision of the friction diminishing region 122, which provides a space of triggering action for retraction of the needle assembly 2, the front hub portion 211 can be pushed forwards relative to the smaller-diameter portion 12 so that the friction between the front hub portion 211 and the smaller-diameter portion 12 to be overcome in the course of retraction of the needle assembly 2 into the accommodation chamber 41 by the coiled spring 52 can be reduced. In other words, the substantially continuing forward movement of the needle seat 21 relative to the smaller-diameter portion 12 after the injection course and its subsequently rearward movement due to retraction of the needle assembly 2 by the coiled spring 52, transform the static friction between the front hub portion 211 and the smaller-diameter portion 12 into a kinetic friction, which can be easily overcome by the predetermined biasing force of the coiled spring 52 in the course of retraction of the needle assembly 2 into the accommodation chamber 41, thereby ensuring successful and smooth retraction of the needle assembly 2.

It is further noted that since the needle seat 21 is in the form of a metal tube, it can be configured to have a relatively small diameter. Thus, the needle cannula 22 can be formed to have a relatively small diameter, as shown in FIGS. 1 to 5, so as to be adapted for injecting medication of a very small volume, such as 1 ml. Likewise, the barrel 1 can be configured to have a smaller diameter with a relatively compensatory elongation of the length of the barrel for a unit medication volume. Thus, the spacing of graduations (not shown) marked on the barrel 1 of extremely small volume, such as 1 cc., and smaller ones, can be relatively large to facilitate accurate reading of the volume of medication in injection course.

Figure 7:
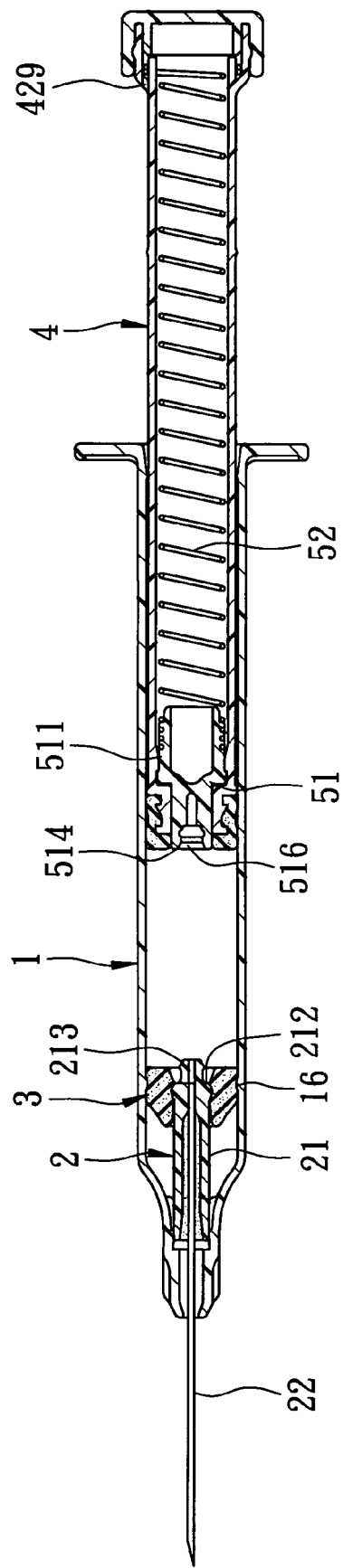
FIG. 7 is a sectional view of the second preferred embodiment of a disposable syringe according to this invention.

Referring to FIG. 7, the second preferred embodiment of a disposable syringe according to this invention is similar to the first preferred embodiment in construction, but is adapted for injecting medication of a general volume, such as 3 ml, 5 ml, or more. That is, the barrel 1, the tubular plunger 4 and the tubular needle seat 21 have relatively large diameters. The tubular needle seat 21 is in the form of a plastic injecting tube, and has a rear anchoring portion 213 which extends rearwardly from the gripped portion 212 along the axis (X). In addition, the coupling member 51 has an anchored portion 514 which has an engaging recess 516 that is configured to grip the rear anchoring portion 213 with a holding force when the needle seat 21 is placed in the retracted position.

Figure 8:
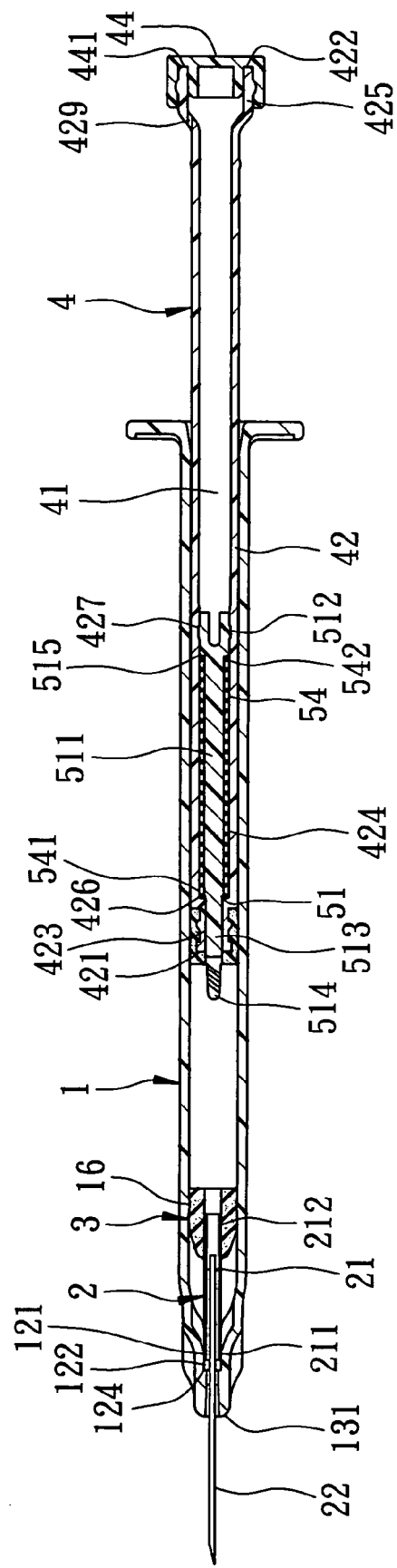
FIGS. 8 and 9 are sectional views of the third preferred embodiment of a disposable syringe according to this invention in a state of use and in a retracted state, respectively.
Figure 9:
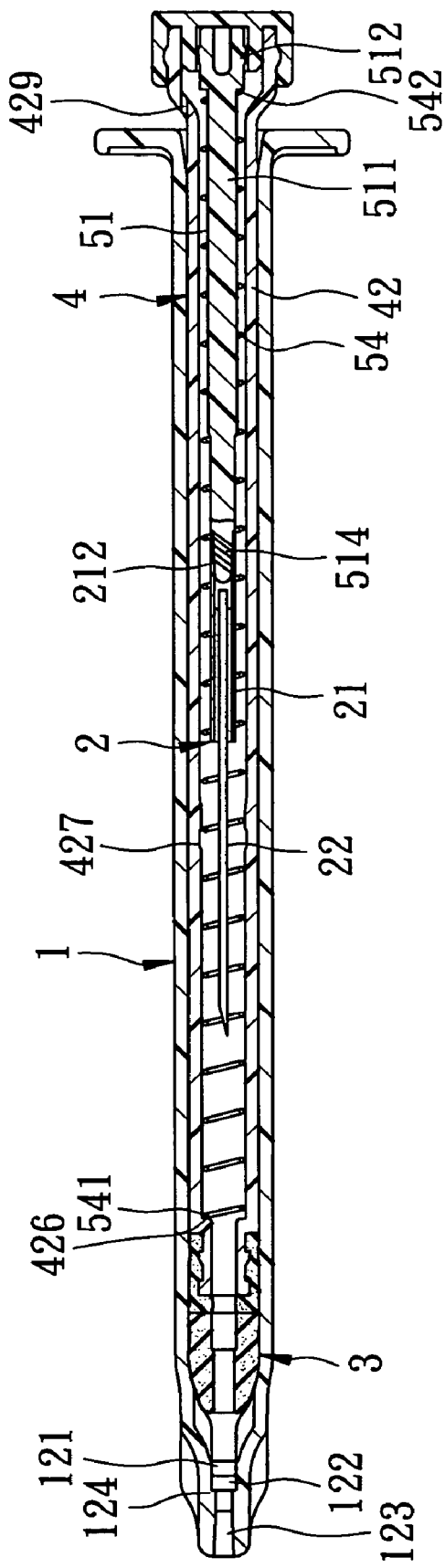

Referring to FIGS. 8 and 9, the third preferred embodiment of a disposable syringe according to this invention is similar to the first preferred embodiment in construction, except that the coupling member 51 has a shank portion 511 which is interposed between the anchored portion 514 and the surrounding retained portion 512. In addition, the intermediate surrounding wall 42 of the tubular plunger 4 and the shank portion 511 respectively have an annular shoulder 426 and a flange 515 which are respectively proximate to the front opened end wall 421 of the plunger 4 and distal from the anchored portion 514 and which are spaced apart from each other in the longitudinal direction so as to define a biasing member receiving space therebetween. The biasing member 54 is a coiled spring which has front and rear spring ends 541,542 abutting against the annular shoulder 426 and the flange 515, respectively, such that the coiled spring is compressed when the surrounding retained portion 512 is in frictional engagement with the annular groove 427 in the intermediate surrounding wall 42 by virtue of the second frictional force.

Figure 10:
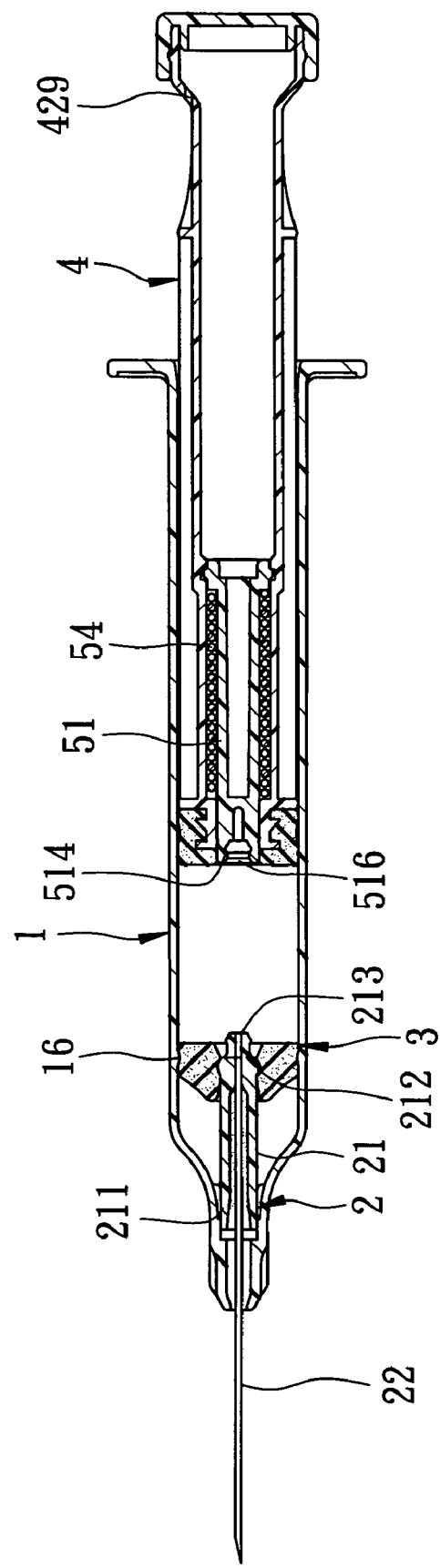
FIG. 10 is a sectional view of the fourth preferred embodiment of a disposable syringe according to this invention.

Referring to FIG. 10, the fourth preferred embodiment of a disposable syringe according to this invention is similar to the third preferred embodiment in construction, but is adapted for injecting medication of a general volume, such as 3 ml, 5 ml, or more. That is, the barrel 1, the tubular plunger 4 and the tubular needle seat 21 have relatively larger diameters. The tubular needle seat 21 is in the form of a plastic injecting tube, and has a rear anchoring portion 213 which extends rearwardly from the gripped portion 212 along the axis (X). In addition, the coupling member 51 has an anchored portion 514 which has an engaging recess 516 which is configured to grip the rear anchoring portion 213 with a holding force when the needle seat 21 is placed in the retracted position.

Figure 11:
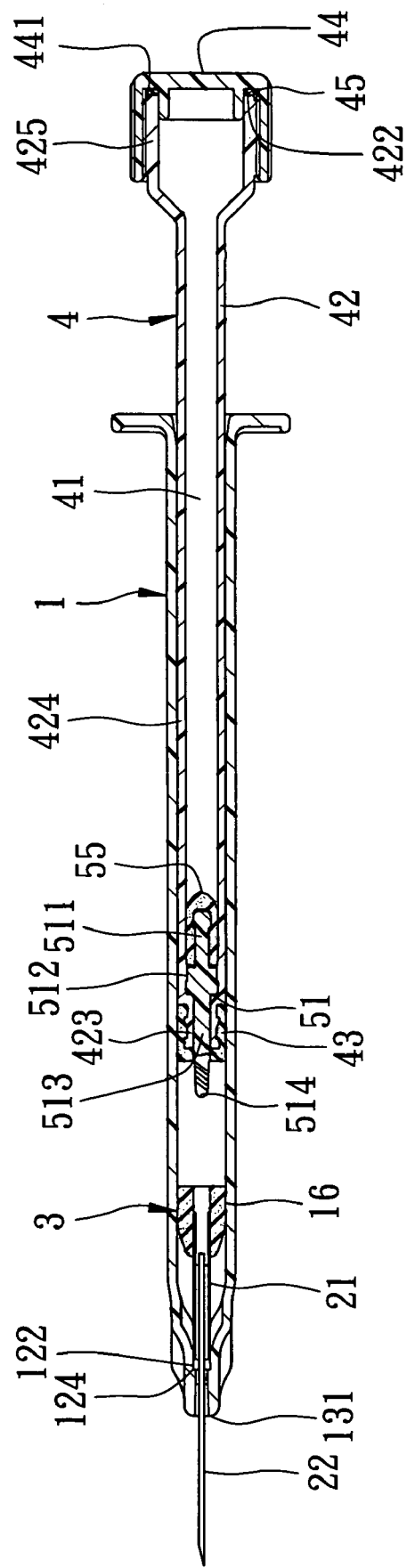
FIG. 11 is a sectional view of the fifth preferred embodiment of a disposable syringe according to this invention in a state of use.
Figure 12:
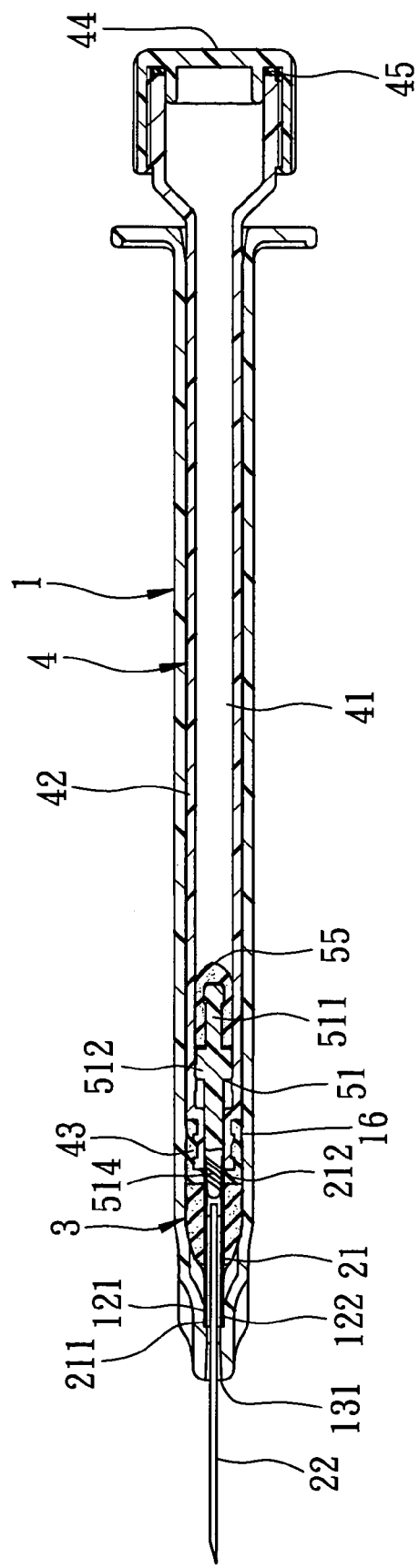
FIG. 12 is a sectional view of the fifth preferred embodiment, showing the state in which a needle seat passes by a friction diminishing region.
Figure 13:
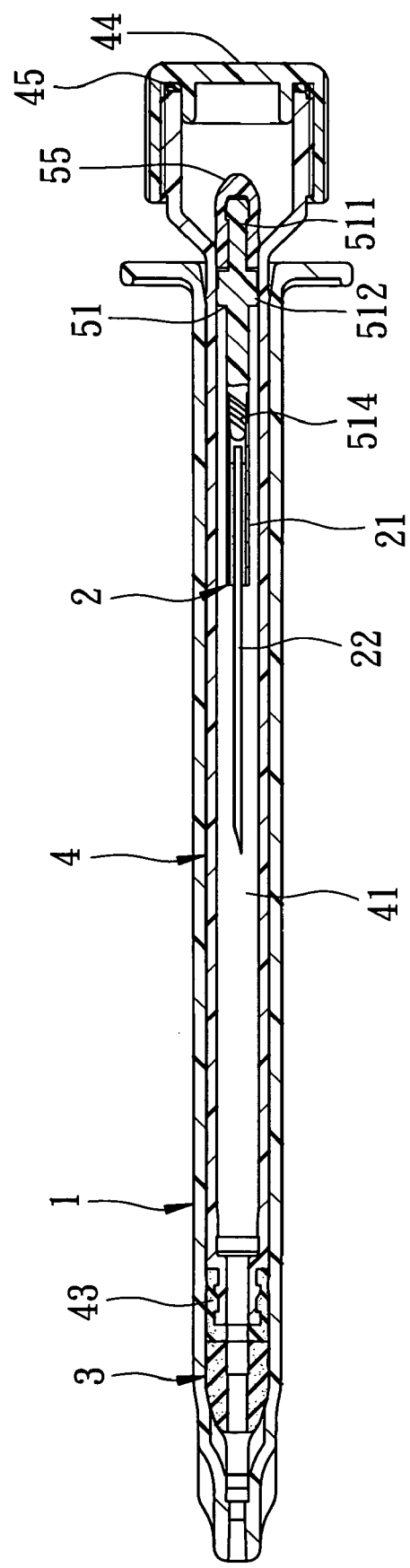
FIG. 13 is a sectional view of the fifth preferred embodiment in a retracted state.

Referring to FIGS. 11 to 13, the fifth preferred embodiment of a disposable syringe according to this invention is similar to the first preferred embodiment in construction. The difference resides in that a seal ring member 45, such as an O-ring, is disposed between the rear opened end wall 422 and the annular groove 441 in the end cap 44 to establish fluid-tight engagement therebetween. The enlarged terminal segment 425 is not formed with the vent hole described in the first preferred embodiment. In addition, instead of the coiled spring 52,54 described above, the biasing member includes a fluid, such as air, which is contained in the accommodation chamber 41 in the tubular plunger 4 at a relatively reduced pressure, and a sealing member 55 which is sleeved on the shank portion 511 of the coupling member 51 to provide a seal between the coupling member 51 and the intermediate surrounding wall 42 so as to trap the fluid in the accommodation chamber 41. Thus, when the surrounding retained portion 512 is released from the intermediate surrounding wall 42, the anchored portion 514 is suctioned to the retracted position due to a pressure difference between the ambient atmosphere and the reduced pressure.

Figure 14:
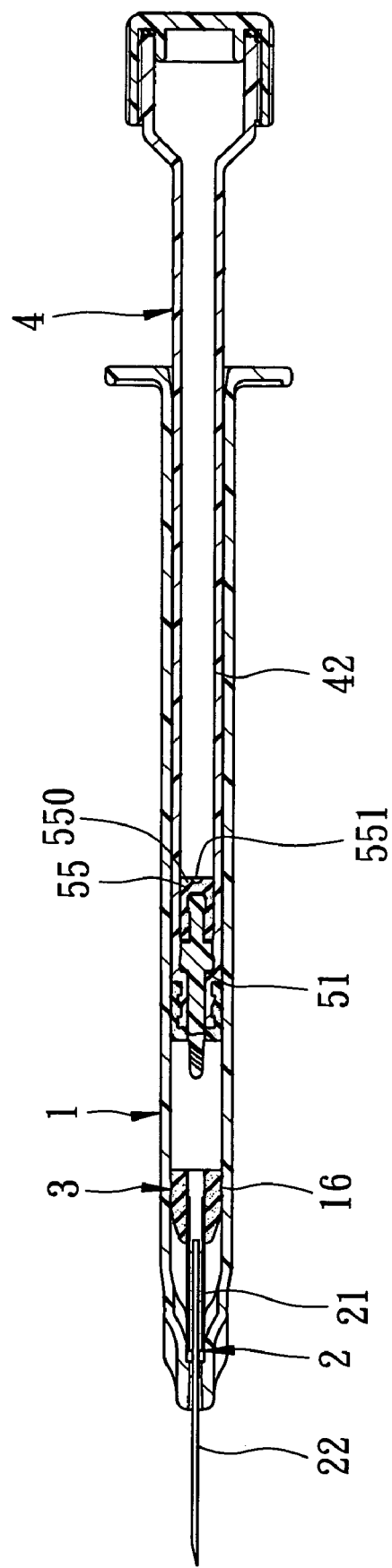
FIGS. 14 and 15 are sectional views of the sixth and seventh preferred embodiments of a disposable syringe according to this invention, respectively.

Further, referring to FIG. 14, in the sixth preferred embodiment of a disposable syringe according to this invention, which is similar to the fifth preferred embodiment, the sealing member 55 extends in the longitudinal direction to terminate at a rear end wall 550 which is disposed rearwardly of the coupling member 51 and which has a central recess 551 extending inwardly and along the axis (X) so as to enhance deformability of the rear end wall 550 in radial directions, thereby enhancing sealing attachment of the sealing member 55 with the intermediate surrounding wall 42.

Figure 15:
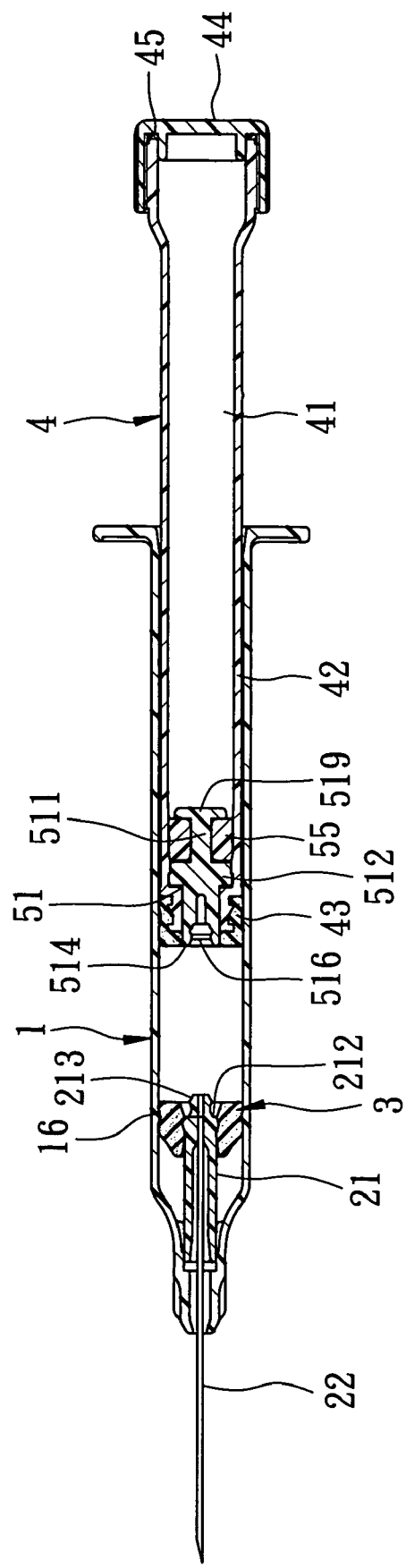

Referring to FIG. 15, the seventh preferred embodiment of a disposable syringe according to this invention is similar to the fifth preferred embodiment in construction, but is adapted for injecting medication of a general volume, such as 3 ml, 5 ml, or more. The tubular needle seat 21 is in the form of a plastic injecting tube, and has a rear anchoring portion 213 which extends rearwardly from the gripped portion 212 along the axis (X) so as to engage an engaging recess 516 in the anchored portion 514 of the coupling member 51 with a holding force when the needle seat 21 is placed in the retracted position. In addition, the coupling member 51 has a shank portion 511 extending rearwardly from the surrounding retained portion 512 to terminate at an enlarged head portion 519. The sealing member 55 is sleeved on the shank portion 511, and is interposed between the head portion 519 and the surrounding retained portion 512 so as to be deformed radially for enhancing the sealing attachment with the intermediate surrounding wall 42.

Figure 16:
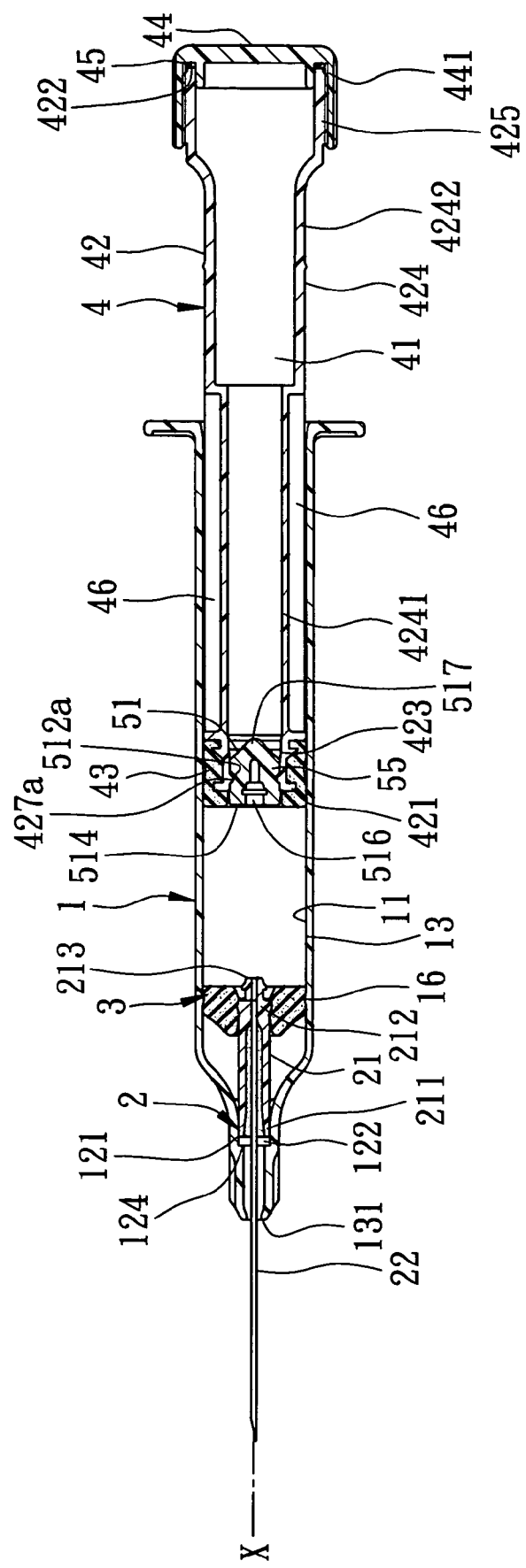
FIGS. 16 and 17 are sectional views of the eighth preferred embodiment of a disposable syringe according to this invention in a state of use and in a retracted state, respectively.
Figure 17:
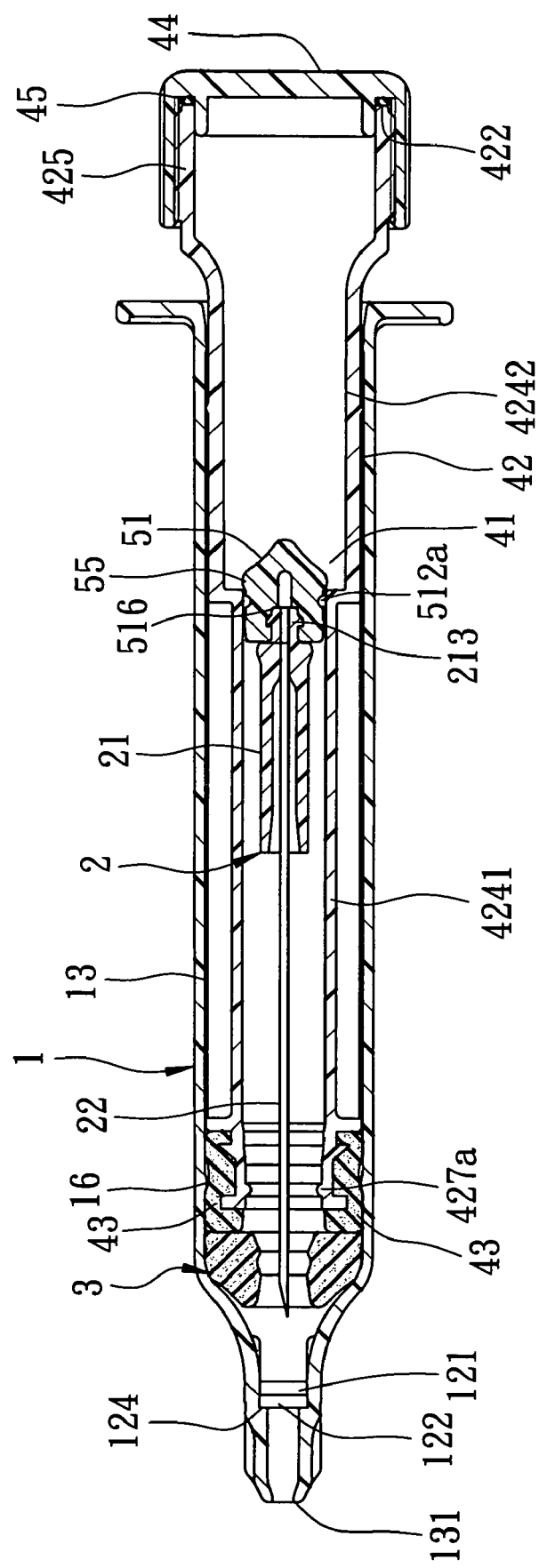

Referring to FIGS. 16 and 17, the eighth preferred embodiment of a disposable syringe according to this invention is similar to the seventh preferred embodiment in construction, and is adapted for injecting medication of a general volume, such as 3 ml, 5 ml, or more. In this embodiment, the larger rear segment 424 of the intermediate surrounding wall 42 of the tubular plunger 4 includes front and rear wall segments 4241, 4242 which are disposed proximate to the front and rear opened end walls 421,422, respectively, and which have smaller and larger outer peripheral surfaces, respectively. The plunger 4 further includes a plurality of rib fins 46 which are formed on the smaller outer peripheral surface of the front wall segment 4241 and which are flush with the larger outer peripheral surface of the rear wall segment 4242 so as to guide movement of the plunger 4 relative to the larger-diameter portion 11 of the inner surrounding barrel surface 13 while minimizing frictional force therebetween. The smaller front segment 423 and the coupling member 51 respectively have an annular protrusion 427a and an annular groove 512a which engage each other to provide the second frictional force. The coupling member 51 further has a tapered rear portion 517 opposite to the engaging recess 516 so as to establish fluid-tight engagement with the smaller front segment 423. The sealing member 55 is formed integrally with the coupling member 51 and is disposed between the tapered rear portion 517 and the annular groove 512a.

When the surrounding retained portion (the annular groove 512a) is released from the intermediate surrounding wall 42 (the annular protrusion 427a), the coupling member 51 is received in the accommodation chamber 41 at the front wall segment 4241, and is held in fluid-tight contact with the front wall segment 4241, thereby facilitating sliding of the coupling member 51, as well as the needle assembly 2, to the retracted position.

Figure 18:
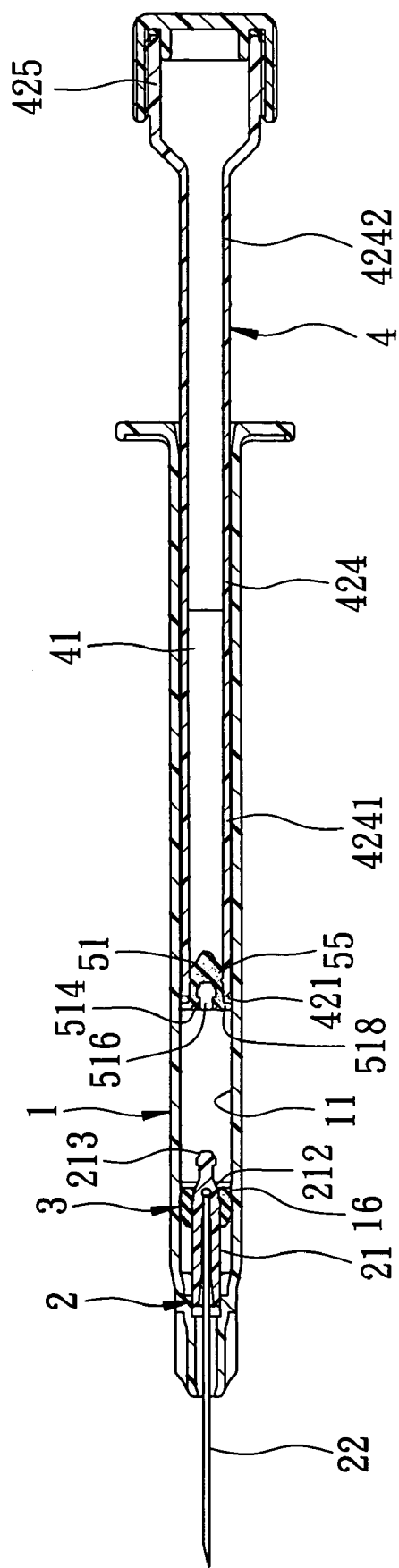
FIG. 18 is a sectional view of the ninth preferred embodiment of a disposable syringe according to this invention in a state of use.
Figure 19:
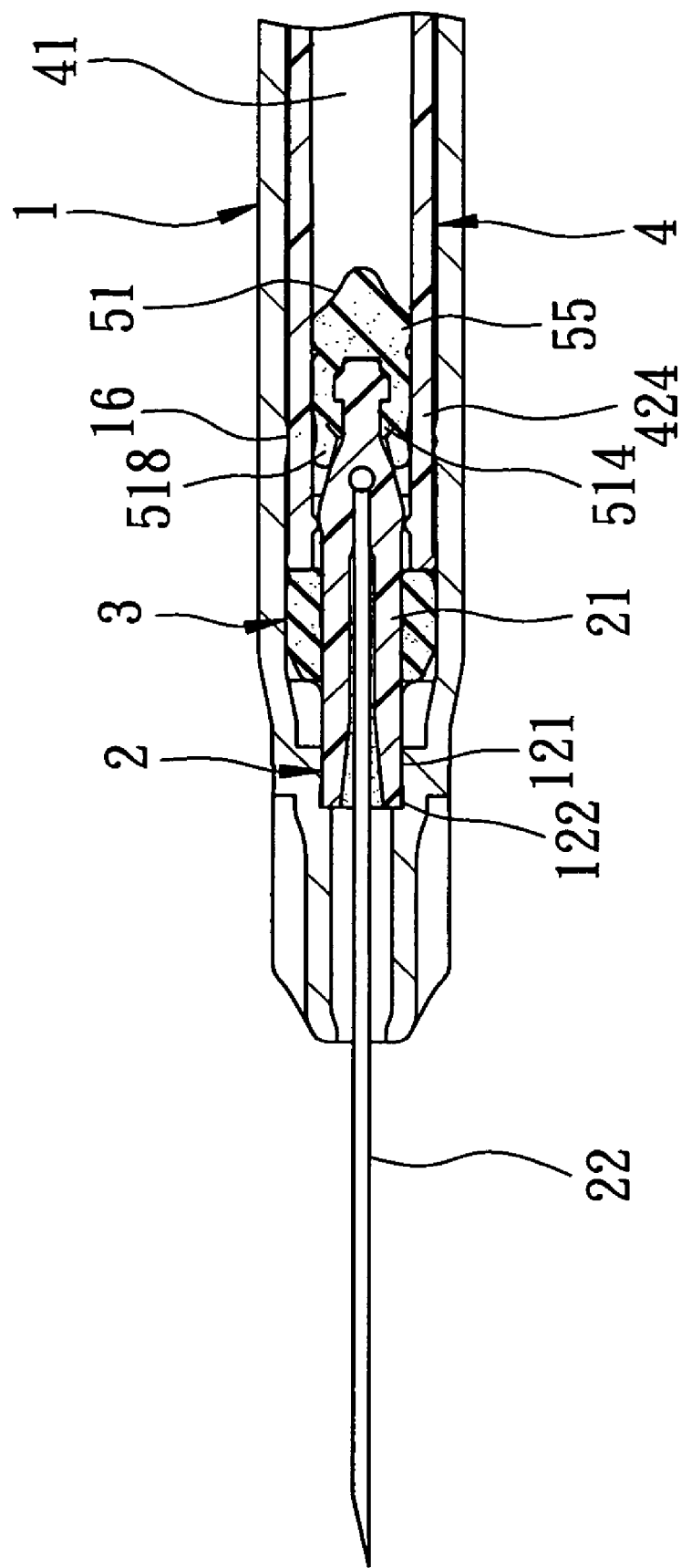
FIG. 19 is a fragmentary sectional view of the ninth preferred embodiment, showing the state in which a needle seat passes by a friction diminishing region.

Referring to FIGS. 18 and 19, the ninth preferred embodiment of a disposable syringe according to this invention is similar to the eighth preferred embodiment in construction, but is adapted for injecting medication of an extremely small injection volume, such as 1 ml. The sealing member 55 is formed integrally with the coupling member 51, is made from a deformable material, and surrounds the anchored portion 514. In addition, the coupling member 51 has an annular front edge 518 which is slidable on and is in fluid-tight engagement with the larger-diameter portion 11 of the barrel 1 so as to serve as the seal ring 43 in the previous preferred embodiment. When the coupling member 51 is placed in the retracted position, the annular front edge 518 is deformed and converged to be retracted into the accommodation chamber 41.

Figure 20:
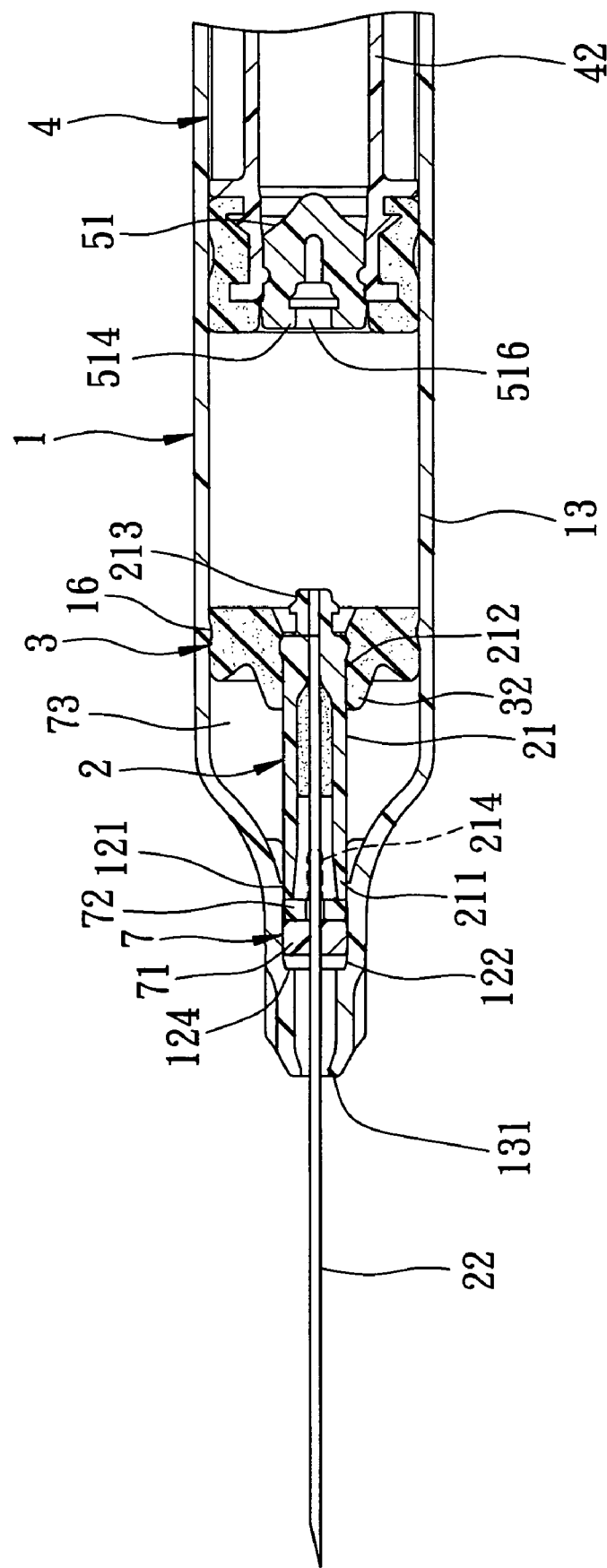
FIG. 20 is a fragmentary sectional view of the tenth preferred embodiment of a disposable syringe according to this invention in a state of use.
Figure 21:
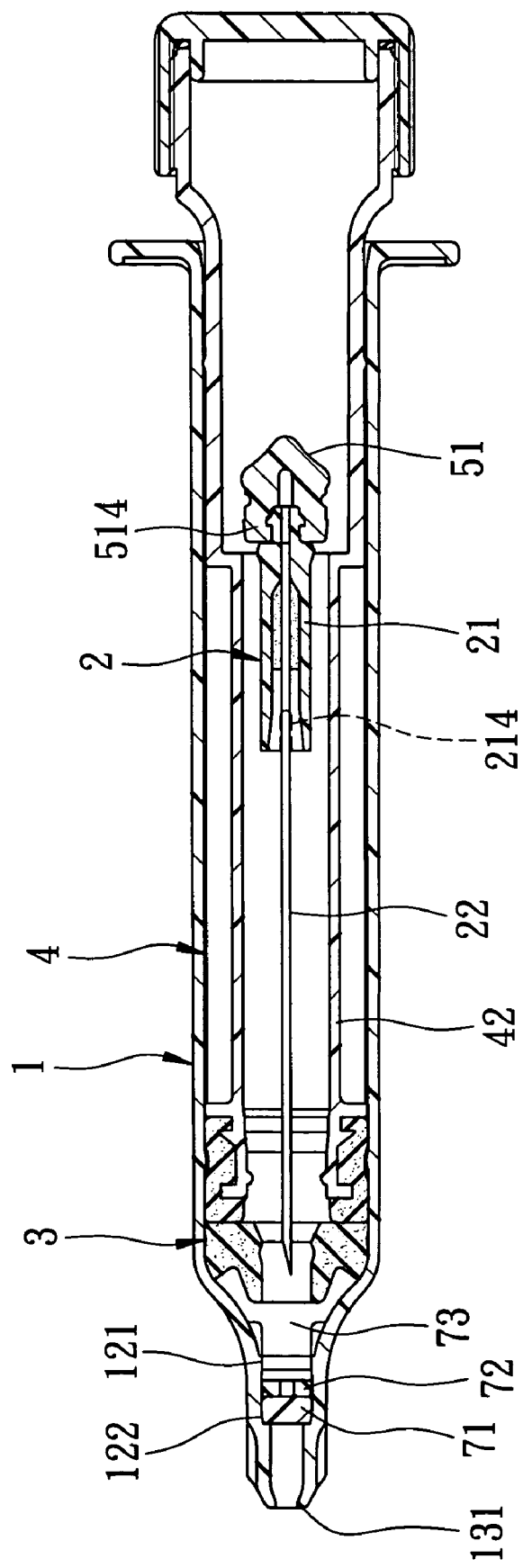
FIG. 21 is a sectional view of the tenth preferred embodiment in a retracted state.
Figure 22:
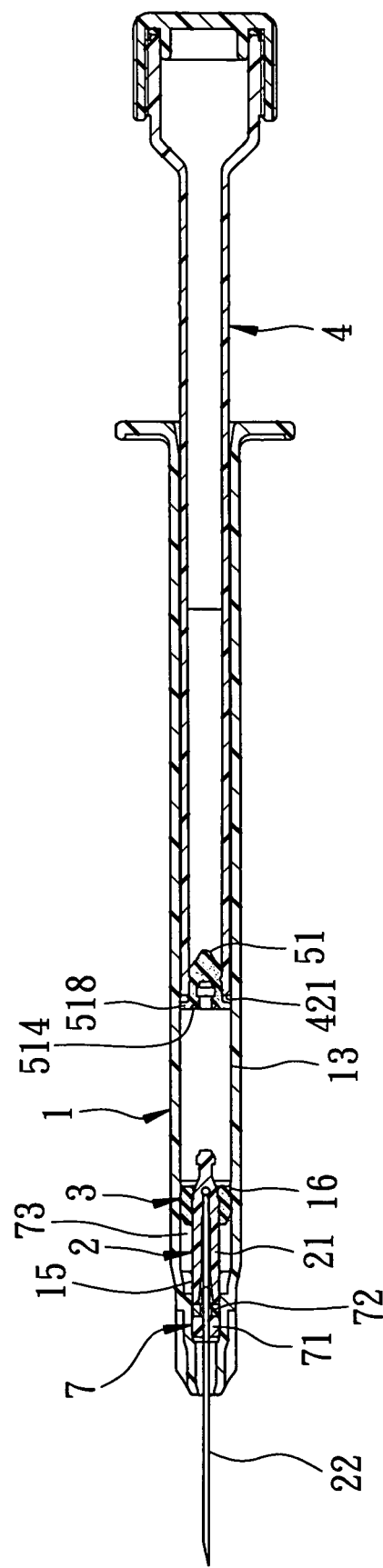
FIGS. 22 to 25 are sectional views of the eleventh, twelfth, thirteenth and fourteenth preferred embodiments of a disposable syringe according to this invention, respectively.
Figure 23:
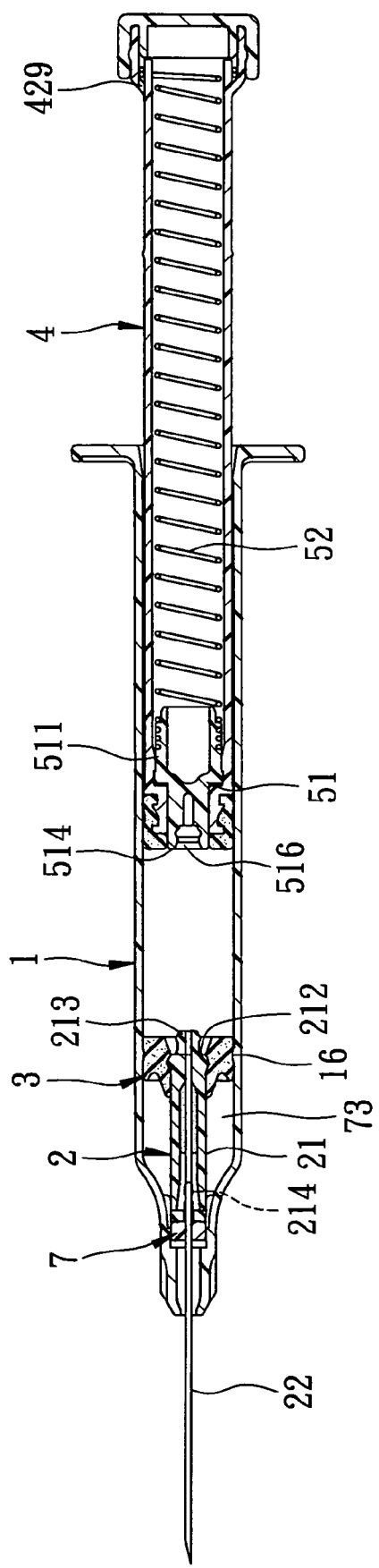
Figure 24:
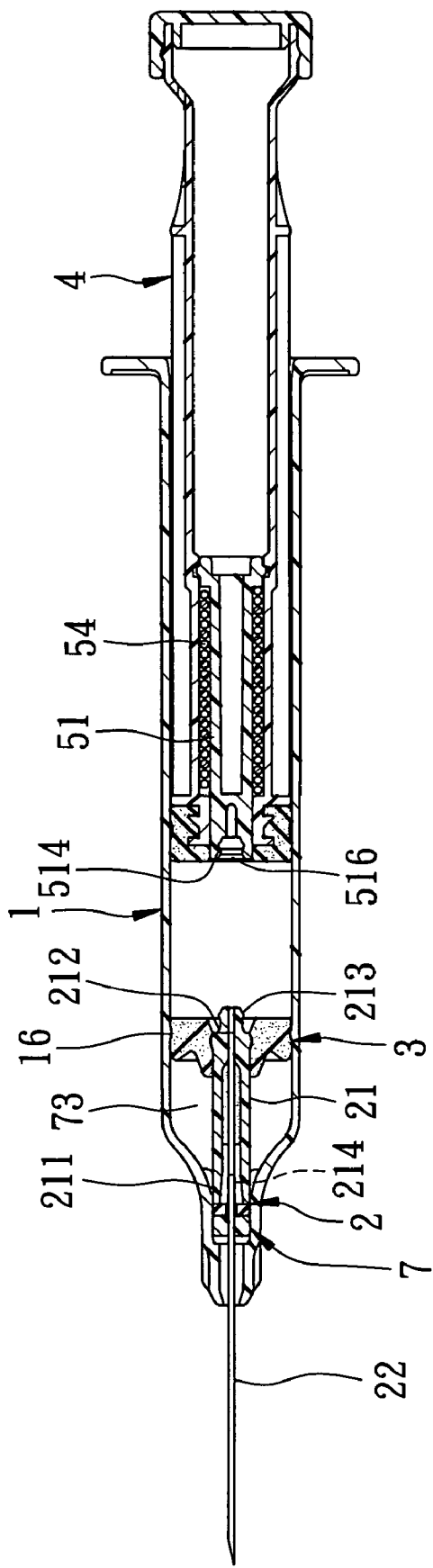
Figure 25:
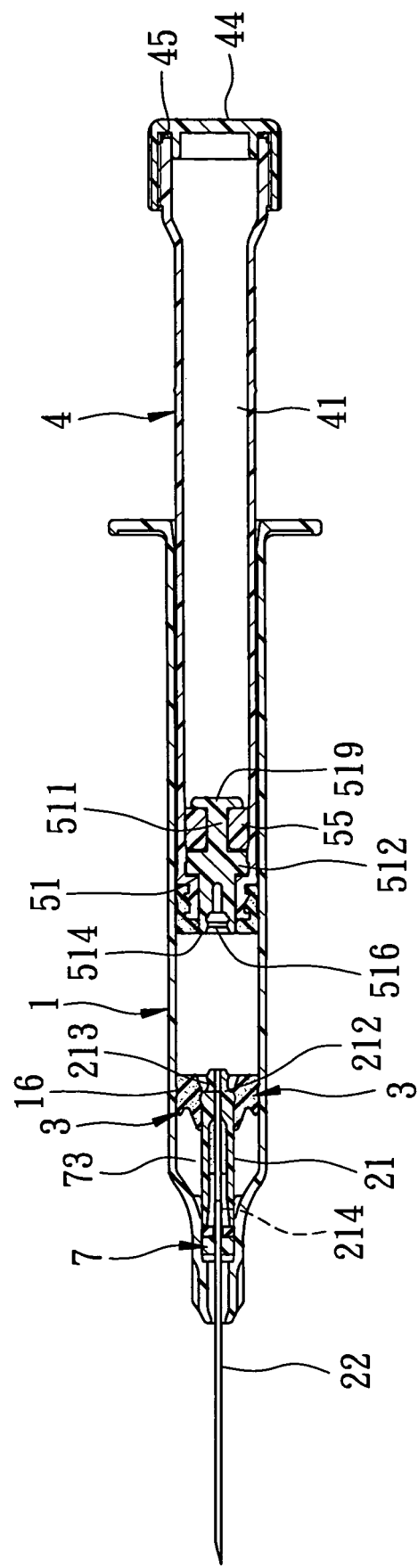

Referring to FIGS. 20 and 21, the tenth preferred embodiment of a disposable syringe according to this invention is similar to the eighth preferred embodiment in construction. In this embodiment, a sealing unit 7 is further disposed to be in fluid-tight engagement with the friction diminishing region 122, and is spaced apart from the shoulder abutment 124 to define a space of triggering action for retraction of the needle assembly 2. The sealing unit 7 includes an elastomeric plug 71 and a ring plate 72 abutting against each other. The tubular grip member 3 is formed with a deformable sealing portion 32 which is in fluid-tight engagement with the gripped portion 212 of the needle seat 21 so as to form a fluid-tight compressible chamber 73. The compressible chamber 73 is filled with a fluid. The front hub portion 211 of the needle seat 21 is disposed to abut against the sealing unit 7, and has a plurality of through holes 214 formed therethrough so as to be in fluid communication with the compressible chamber 73. Thus, when the tubular grip member 3 is pushed forwardly by virtue of forward movement of the plunger 4 to move the front hub portion 211 past the friction diminishing region 122, the fluid in the compressible chamber 73 is squeezed through the through holes 214, thereby generating a pressure force in the longitudinal direction that depresses the surrounding gripped portion 212 rearwardly to help thrust the anchored portion 514 rearward to the retracted position.

Referring to FIGS. 22 to 25, the eleventh, twelfth, thirteenth and fourteenth preferred embodiments of a disposable syringe according to this invention are respectively similar to the ninth, second, fourth and sixth preferred embodiments in construction. Besides, in each of these embodiments, the disposable syringe further comprises a sealing unit 7 which is the same as that of the tenth preferred embodiment, and which is disposed to be in fluid-tight engagement with the friction diminishing region 122.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

We claim:

1. A disposable syringe comprising:
    a needle cannula;
    a tubular needle seat including a front hub portion which is disposed to fix said needle cannula therein, a gripped portion which extends from said front hub portion in a longitudinal direction, and a rear anchoring portion which is disposed opposite to said front hub portion in the longitudinal direction;
    a barrel having an inner surrounding barrel surface which surrounds an axis in the longitudinal direction and which defines a passage therein, said passage having rearward and forward openings which are disposed opposite to each other in the longitudinal direction, said inner surrounding barrel surface including a larger-diameter portion and a smaller-diameter portion which are disposed proximate to said rearward and forward openings, respectively, said larger-diameter portion having a retaining area which is spaced apart from said smaller-diameter portion in the longitudinal direction, said smaller-diameter portion including a retaining region which is disposed proximate to said larger-diameter portion and which is configured to retain said front hub portion thereat when said needle seat is in a position of use, and a friction diminishing region which extends from said retaining region toward said forward opening and which terminates at a shoulder abutment, said shoulder abutment defining a communicating hole which permits passage of said needle cannula therethrough, and being spaced apart from said front hub portion along the axis in the position of use;

a tubular grip member which, in the position of use, is disposed to bring said gripped portion into engagement with said retaining area by virtue of a first frictional force generated therebetween;

a tubular plunger which is disposed to be movable in said passage along said larger-diameter portion, said plunger having a front opened end wall which is movable to abut against said grip member, a rear opened end wall which is disposed opposite to said front opened end wall and which extends outwardly of said rearward opening so as to be manually operable, and an intermediate surrounding wall which is interposed between said front and rear opened end walls and which defines an accommodation chamber;

a coupling member having a surrounding retained portion which surrounds the axis and which is disposed in said accommodation chamber to be in frictional engagement with said intermediate surrounding wall by virtue of a second frictional force, and an anchored portion which is disposed adjacent to said front opened end wall in the position of user which confronts said rear anchoring portion, and which is engageable with said rear anchoring portion by a holding force when said coupling member is moved forwardly towards said forward opening such that, when said grip member is pushed forward by virtue of forward movement of said plunger against the first frictional force to cause said front hub portion to move past said friction diminishing region to abut against said shoulder abutment, a pushing force subsequently applied to said plunger causes said anchored portion to rub against said rear anchoring portion, which remains unmoved in place due to engagement of said front hub portion with said shoulder abutment, so that said anchored portion is engaged with said rear anchoring portion and is moved relative to said intermediate surrounding wall towards said rear opened end wall so as to release said surrounding retained portion from said intermediate surrounding wall, thereby enabling said anchored portion to be moved from the position of use to a retracted position where said anchored portion is disposed closer to said rear opened end wall and where said needle seat and said needle cannula are received in said accommodation chamber; and a biasing member disposed to bias said anchored portion towards the retracted position.

2. The disposable syringe of claim 1, wherein said passage at said friction diminishing region has a diameter larger than that of said passage at said retaining region.

3. The disposable syringe of claim 1, wherein said tubular needle seat is in form of a metal tube which includes a front segment to serve as said front hub portion, and a rear segment that is opposite to said front segment in the longitudinal direction and that has outer and inner segment surfaces opposite to each other in radial directions relative to the axis, said outer and inner segment surfaces being configured to serve as said gripped portion and said rear anchoring portion, respectively.

4. The disposable syringe of claim 1, wherein said intermediate surrounding wall of said tubular plunger has a smaller front segment and a larger rear segment disposed proximate to said front and rear opened end walls, respectively, and an enlarged terminal segment disposed between said larger rear segment and said rear opened end wall.

5. The disposable syringe of claim 4, wherein said enlarged terminal segment has a vent hole in fluid communication with the ambient atmosphere.

6. The disposable syringe of claim 5, wherein said coupling member has a shank portion which extends from said surrounding retained portion distal from said anchored portion, said biasing member including a coiled spring which has a front spring end that engages said shank portion, and a rear spring end that is retained to said rear opened end wall such that said coiled spring is tensioned when said surrounding retained portion is in frictional engagement with said intermediate surrounding wall by virtue of the second frictional force.

7. The disposable syringe of claim 6, wherein said larger rear segment has an annular rib which is disposed thereon proximate to said rear opened end wall, said rear spring end of said coiled spring being retained by said annular rib.

8. The disposable syringe of claim 5, wherein said coupling member has a shank portion which is interposed between said anchored portion and said surrounding retained portion, said intermediate surrounding wall and said shank portion respectively having an annular shoulder and a flange which are respectively proximate to said front opened end wall and distal from said anchored portion and which are spaced apart from each other in the longitudinal direction so as to define a biasing member receiving space therebetween, said biasing member being a coiled spring which has front and rear spring ends abutting against said annular shoulder and said flange, respectively, such that said coiled spring is compressed when said surrounding retained portion is in frictional engagement with said intermediate surrounding wall by virtue of the second frictional force.

9. The disposable syringe of claim 1, wherein said rear anchoring portion extends rearwardly from said gripped portion along the axis, said anchored portion having an engaging recess which is configured to grip said rear anchoring portion with the holding force when said needle seat is to be placed in the retracted position.

10. The disposable syringe of claim 1, further comprising an end cap disposed to cover said rear opened end wall, and a seal ring member which is disposed to establish fluid-tight engagement between said end cap and said rear opened end wall.

11. The disposable syringe of claim 10, wherein said biasing member includes a fluid which is contained in said accommodation chamber at a reduced pressure, and a sealing member which is configured to provide a sealing between said coupling member and said intermediate surrounding wall so as to trap said fluid in said accommodation chamber such that when said surrounding retained portion is released from said intermediate surrounding wall, said anchored portion is suctioned to the retracted position due to a pressure difference between the ambient atmosphere and the reduced pressure.

12. The disposable syringe of claim 11 wherein said sealing member extends in the longitudinal direction to terminate at a rear end wall which is disposed rearwardly of said coupling member and which has a central recess extending inwardly and along the axis so as to enhance deformability of said rear end wall in radial directions, thereby enhancing sealing attachment of said sealing member with said intermediate surrounding wall.

13. The disposable syringe of claim 11, wherein said coupling member has a shank portion extending rearwardly from said surrounding retained portion to terminate at an enlarged head portion, said sealing member being sleeved on said shank portion and being interposed between said head portion and said surrounding retained portion so as to be deformed radially for enhancing sealing attachment of said sealing member with said intermediate surrounding wall.

14. The disposable syringe of claim 11, wherein said sealing member surrounds the axis, and is formed integrally with said coupling member.

15. The disposable syringe of claim 11, wherein said sealing member is formed integrally with said coupling member, is made from a deformable material, and surrounds said anchored portion, said coupling member having an annular front edge which is slidable on and is in fluid-tight engagement with said larger-diameter portion of said inner surrounding barrel surface.

16. The disposable syringe of claim 1, further comprising a sealing unit which is in fluid-tight engagement with said friction diminishing region, said tubular grip member being formed with a deformable sealing portion which is in fluid-tight engagement with said gripped portion of said needle seat so as to form a fluid-tight compressible chamber, said compressible chamber being filled with a fluid, said front hub portion of said needle seat having a plurality of through holes formed therethrough so as to be in fluid communication with said compressible chamber, such that when said tubular grip member is pushed forwardly by virtue of forward movement of said plunger to move said front hub portion past said friction diminishing region, said fluid in said compressible chamber is squeezed through said through holes, thereby generating a pressure force in the longitudinal direction that depresses said surrounding gripped portion rearwardly to help thrust said anchored portion to the retracted position.

17. The disposable syringe of claim 1, wherein said inner surrouding barrel surface of said barrel further includes an annular shoulder disposed between said larger-diameter portion and said smaller-diameter portion, and a plurality of ribs formed on said annular shoulder.

18. The disposable syringe of claim 1, wherein said coupling member further has a retained shank portion which is disposed between said surrounding retained portion and said anchored portion and which extends in said accommodation chamber at said smaller front segment so at to stabilize said coupling member at said smaller front segment.

* * * * *